(12) United States Patent
Eldaly et al.

(10) Patent No.: US 12,329,537 B2
(45) Date of Patent: Jun. 17, 2025

(54) SYSTEM AND METHOD FOR MEASUREMENT AND ASSESSMENT OF DEPTH OF ANESTHESIA IN AN ANIMAL SUBJECT BASED ON ELECTROENCEPHALOGRAPHY

(71) Applicant: City University of Hong Kong, Hong Kong (HK)

(72) Inventors: Abdelrahman Bakr Mohammed Abdelnaby Eldaly, Hong Kong (HK); Mehdi Hasan Chowdhury, Hong Kong (HK); Stephen Kugbere Agadagba, Hong Kong (HK); Ray Chak Chung Cheung, Hong Kong (HK); Leanne Lai Hang Chan, Hong Kong (HK)

(73) Assignee: City University of Hong Kong, Hong Kong (HK)

( * ) Notice: Subject to any disclaimer, the term of this patent is extended or adjusted under 35 U.S.C. 154(b) by 383 days.

(21) Appl. No.: 17/482,413

(22) Filed: Sep. 22, 2021

(65) Prior Publication Data
US 2023/0102090 A1 Mar. 30, 2023

(51) Int. Cl.
A61B 5/00 (2006.01)
A61B 5/372 (2021.01)
A61B 5/374 (2021.01)

(52) U.S. Cl.
CPC ............ *A61B 5/4821* (2013.01); *A61B 5/374* (2021.01); *A61B 5/7225* (2013.01); *A61B 5/7264* (2013.01)

(58) Field of Classification Search
CPC ..... A61B 5/4821; A61B 5/374; A61B 5/7225; A61B 5/7264; A61B 5/725
See application file for complete search history.

(56) References Cited

U.S. PATENT DOCUMENTS

| | | | |
|---|---|---|---|
| 8,666,484 B2 * | 3/2014 | Nierenberg | A61B 5/369 600/544 |
| 2014/0289172 A1 * | 9/2014 | Rothman | A61B 5/369 706/11 |
| 2020/0253544 A1 * | 8/2020 | Belur Nagaraj | A61B 5/4821 |

FOREIGN PATENT DOCUMENTS

| | | |
|---|---|---|
| CN | 103637798 B | 3/2016 |
| CN | 206120315 U | 4/2017 |

(Continued)

OTHER PUBLICATIONS

Delorme A, Makeig S. Eeglab: an open source toolbox for analysis of single-trial EEG dynamics including independent component analysis. J Neurosci Methods. Mar. 15, 2004;134(1):9-21. doi: 10.1016/j.jneumeth.2003.10.009. PMID: 15102499. (Year: 2004).*

(Continued)

*Primary Examiner* — Etsub D Berhanu
(74) *Attorney, Agent, or Firm* — Idea Intellectual Limited; Margaret A. Burke; Sam T. Yip

(57) ABSTRACT

The present invention provides a system for implementing a logistic regression classification mechanism to measure and assess a depth of anesthesia of an animal subject based on electroencephalography (EEG), which includes a signal pre-processor, an epoch generator, a feature extractor, a classifier, and a predictor. Related method of how to pre-process the raw data of EEG signal, epoch generation thereof, feature extraction from each epoch, classification based on extracted features, and prediction of different states of the animal subject based on a prediction decision mechanism is also provided. Classification accuracy of the present invention for 1-second and 10% overlapping epochs is about 94% with an average total system delay of about 12 μs and low on-chip power consumption. The present system is entirely optimized, which leads to a 100% accurate channel prediction after a 7-second run-time on average.

6 Claims, 11 Drawing Sheets

(56) References Cited

FOREIGN PATENT DOCUMENTS

| CN | 108451527 A | 8/2018 | | |
|---|---|---|---|---|
| WO | WO-2004005895 A1 | * | 1/2004 | ............ A61B 5/0059 |
| WO | 2019041772 A1 | | 3/2019 | |
| WO | 2019127558 A1 | | 7/2019 | |

OTHER PUBLICATIONS

Mux. (2006). MathWorks. Retrieved Dec. 4, 2023, from https://www.mathworks.com/help/simulink/slref/mux. (Year: 2006).*

Tabassum et al. Novel Multirate Digital Filter for EEG on FPGA. 2nd International Conference on Electrical&Electronic Engineering(ICEEE), Dec. 19-21, 2017, Ruet. (Year: 2017).*

Q. Liu et al., "Sample entropy analysis for the estimating depth of anaesthesia through human EEG signal at different levels of unconsciousness during surgeries," PeerJ, vol. 2018, No. 5, pp. 1-25, 2018.

S. B. Nagaraj et al., "Electroencephalogram Based Detection of Deep Sedation in ICU Patients Using Atomic Decomposition," IEEE Transactions on Biomedical Engineering, vol. 65, No. 12, pp. 2684-2691, 2018.

A. Shalbaf et al., "Monitoring the depth of anesthesia using a new adaptive neurofuzzy system," IEEE Journal of Biomedical and Health Informatics, vol. 22, No. 3, pp. 671-677, 2018.

U. Ha et al., "An EEG-NIRS Multimodal SoC for Accurate Anesthesia Depth Monitoring," IEEE Journal of Solid-State Circuits, vol. 53, No. 6, pp. 1830-1843, 2018.

F. H. Khan et al., "A patient-specific machine learning based EEG processor for accurate estimation of depth of anesthesia," in 2018 IEEE Biomedical Circuits and Systems Conference (BioCAS). IEEE, 2018, pp. 1-4.

W. Saadeh et al., "Design and Implementation of a Machine Learning Based EEG Processor for Accurate Estimation of Depth of Anesthesia," IEEE Transactions on Biomedical Circuits and Systems, vol. 13, No. 4, pp. 658-669, 2019.

Y. G. Yoon et al., "Monitoring the depth of anesthesia from rat EEG using modified Shannon entropy analysis," Proceedings of the Annual International Conference of the IEEE Engineering in Medicine and Biology Society, EMBS, No. 2, pp. 4386-4389, 2011.

J. Kortelainen et al., "EEG-based detection of awakening from isoflurane anesthesia in rats," Proceedings of the Annual International Conference of the IEEE Engineering in Medicine and Biology Society, EMBS, No. Jul. 2014, pp. 4279-4282, 2012.

J. Xu et al., "Brain activity analysis of rat based on electroencephalogram complexity under general anesthesia," in International Conference on Natural Computation. Springer, 2005, pp. 376-385.

Mehdi Hasan Chowdhury et al., "Machine Learning Based Hardware Architecture for DOA Measurement from Mice EEG" in IEEE Transactions on Biomedical Engineering, vol. 69, No. 1, pp. 314-324, Jan. 2022.

* cited by examiner

SYSTEM AND METHOD FOR MEASUREMENT AND ASSESSMENT OF DEPTH OF ANESTHESIA IN AN ANIMAL SUBJECT BASED ON ELECTROENCEPHALOGRAPHY

FIELD OF THE INVENTION

The present invention relates to a system for implementing a logistic regression classification mechanism to measure and assess a depth of anesthesia (DOA) of an animal subject based on electroencephalography (EEG). Related method of how to pre-process the raw data of EEG signal, epoch generation thereof, feature extraction from each epoch, classification based on extracted features, and prediction of different states of the animal subject based on a prediction decision mechanism is also provided.

BACKGROUND

Many surgical operations will become impractical if a subject of the surgery is not in a proper anesthetic state. Therefore, anesthesia is essential in many surgical operations involving relatively highly invasive procedures. Drug-induced anesthesia is commonly used in surgical operations, during which the subject is unresponsive to painful stimuli, thus a precise level of sedation should be maintained to ensure a successful operation, because underdosing or overdosing anesthetics to the subject can cause different problems during and/or post-surgery.

Conventional techniques to evaluate the subject's physiological state during anesthesia includes monitoring blood pressure and heart-rate, change in respiratory patterns, ability to respond to verbal commands, eyelash reflex, pupillary responses, etc. These parameters are used to estimate the depth of anesthesia (DOA). DOA is a measure of consciousness of a subject based on electroencephalography (EEG) of a subject, which is a record of the electrical activity of the subject's central nervous system.

However, conventional assessment of DOA based on a subject's EEG still lies upon anesthesiologist's judgment based on his/her experience because there is no mathematical assessment method in place. In addition, sometimes these bio-physiological factors may be compromised by the subject's pre-existing conditions or vary based on the nature of surgery performed and/or side effects of the medications involved during and/or even pre- or post-surgical operation, leading to unavoidable bias and thereby affecting the accuracy of the evaluation.

Recent studies focused mainly on finding the correlation pattern between human EEG and DOA using certain kinds of machine learning techniques such as Field Programmable Gate Array (FPGA), random forest, support vector machine (SVM), adaptive neural-based fuzzy inference system (ANFIS), deep neural network (DNN), simple decision tree, fine decision tree, modified Shannon entropy, Bayesian information criterion, Lempel-Ziv complexity, etc. Among all these state-of-art, DOA classification accuracy varies from 79% to 93%. Most of them are simply algorithms without an actual machinery to measure and assess the DOA of a subject. Even there is a conventional system to implement an algorithm of these, it is configured to measure EEG of a human being, which is applicable to other animals.

Therefore, there is a need for an actual system implementing a simple and feasible method to measure and assess anesthesia in a wide variety of animals particularly in the field of veterinary medicine/surgery.

SUMMARY OF THE INVENTION

Accordingly, a first aspect of the present invention provides a system for measuring and assessing anesthesia of an animal subject based on electroencephalography, where the system includes:
 a signal pre-processor comprising at least two filters in different filtering frequency and a down-sampler for removing unwanted signals and noise from incoming signal stream of the system to generate an incoming signal for subsequent epoch generation;
 an epoch generator for generating an epoch signal containing 1-second and 10% overlapping epochs comprising a two-input multiplexer, an address generator and a memory, the two-input multiplexer receiving the incoming signal from the signal pre-processor and also a selector input from the address generator to feed an input signal stream to the memory after a counter value of a counter at a relatively higher frequency from the address generator reaches 500; the address generator having two counters at different frequencies and generating two counter signals with write address and read address, respectively, to be fed to the memory, and also a control signal to be fed directly for subsequent feature extraction; the memory receiving the input signal stream from the two-input multiplexer and two counter signals with the write address and read address, respectively, from the address generator and then generating the epoch signal containing the 1-second and 10% overlapping epochs for subsequent feature extraction;
 a feature extractor comprising a derivative calculator and a variance calculator, the derivative calculator receiving the epoch signal containing 1-second and 10% overlapping epochs from the memory of the epoch generator and calculating a mean of accumulated squared-differences among different epochs; the variance calculator receiving absolute value of each of the epochs accumulated and determining a mean of the accumulated epochs, obtaining a deviation of an epoch by subtracting the mean from one of the absolute values of the epoch, calculating a squared deviation followed by determining square root of an average squared deviation for subsequent classification;
 a classifier comprising two cascaded units for expanding features extracted by the feature extractor by double the number of the features followed by feature mapping to set a classification boundary, and subsequently using an output of the feature mapping to obtain a sigmoid function as a decision boundary in order for subsequent prediction;
 a predictor comprising a predictor circuit for accumulating the classifier's outputs, constraining a decision value of the classifier's outputs between 0 and 1, and determining level of anesthesia of the animal subject in terms of the constrained decision value based on the animal subject's real-time electroencephalogram.

In an embodiment, a first filter of the signal pre-processor has a filtering frequency to compensate the power-line interference of the incoming signal from the electroencephalography of the animal subject.

In an embodiment, a second filter of the signal pre-processor has a filtering frequency comparable to an average frequency of a wide electroencephalography frequency region (e.g., 0-250 Hz) of the incoming signal from the animal subject.

The incoming signal can be down sampled at least ten times after being subject to the second filter.

In an embodiment, the epoch generator creates a sliding window to divide each electroencephalography channel into short-overlapped epochs. It is optimally designed to consume lower resources and the smallest possible size of memory unit (RAM).

In an embodiment, the derivative calculator of the feature extractor comprises a multiplier to square the differences among different epochs before calculating the mean of the accumulated squared-differences, and further comprises an accumulator and divisor for calculating the mean.

In an embodiment, the variance calculator comprises a multiplier, an accumulator and a divisor circuit to consecutively calculate the average squared deviation; the variance calculator further comprises a register to store the average squared deviation for being fed to the classifier subsequently.

In an embodiment, the two cascaded units of the classifier comprises a feature mapping unit for said expanding and feature mapping to enhance classification accuracy by setting the classification boundary with an increase in classifier variance, and an exponential and reciprocal computation circuit for receiving the output of the feature mapping unit to determine the sigmoid function as the decision boundary for being fed to the subsequent predictor.

In an embodiment, the predictor is the final subsystem of the present system. It accumulates the level of anesthesia in terms of percentage, and also constrains an output value as a decision score between 0 and 1 with respect to the percentage of the anesthesia of the animal subject, where a 100% anesthetized case will have the decision score of 1, while a 0% anesthetized, i.e., an awake case, will have a score of 0. It overcomes the relatively lower accuracy of the classifier subsystem and introduces accurate, confident, and real-time prediction.

A second aspect of the present invention provides a method for determining depth of anesthesia of an animal subject from a transient behavior of an electroencephalography thereof, where the method includes:
  recording electroencephalographic (EEG) signal of the animal subject and filtering thereof within a relatively lower frequency band to remove unwanted signals and noise;
  down-sampling the filtered EEG signal to at least ten times for reducing data size and accelerating subsequent processing without losing essential features of the EEG for subsequent classification;
  generating epochs from the down-sampled EEG signals comprising segmenting each EEG channel with a shortened signal time and overlapping one EEG signal with a preceding EEG signal thereof;
  extracting two features from each epoch selected from derivative and variance thereof;
  mapping the derivative and variance features to determine a classification boundary followed by using an output of the mapping to determine a sigmoid function as a decision boundary between awake and anesthetized states:
    if the output value is lower than 0.5, the epoch is classified as awake; otherwise, the epoch is classified as anesthetized;
  accumulating the output value of consecutive awake and anesthetized epochs, respectively, and constraining each of the output value between 0 and 1 in order to predict a likelihood of a successive awake or anesthetized epoch.

Classification accuracy of the present invention for 1-second and 10% overlapping epochs is about 94% (after 7-second run-time on average, the prediction accuracy is 100%) with an average total system delay of about 12 μs and low on-chip power consumption. The DOA performance, sensitivity and specificity of the present invention make it a potential DOA measurement tool for veterinary medicine and surgery requiring real-time measurement and assessment of anesthesia of any animal subjects, for example, rodents, felines, canines, bovines, etc.

BRIEF DESCRIPTION OF THE DRAWINGS

Embodiments of the invention are described in more details hereinafter with reference to the drawings, in which.

DETAILED DESCRIPTION OF THE INVENTION

In the following description, systems, devices, methods of, and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

It should be apparent to practitioner skilled in the art that the foregoing and subsequent examples of the system and method are only for the purposes of illustration of working principle of the present invention. It is not intended to be exhaustive or to limit the invention to the precise forms disclosed.

Figure 1:
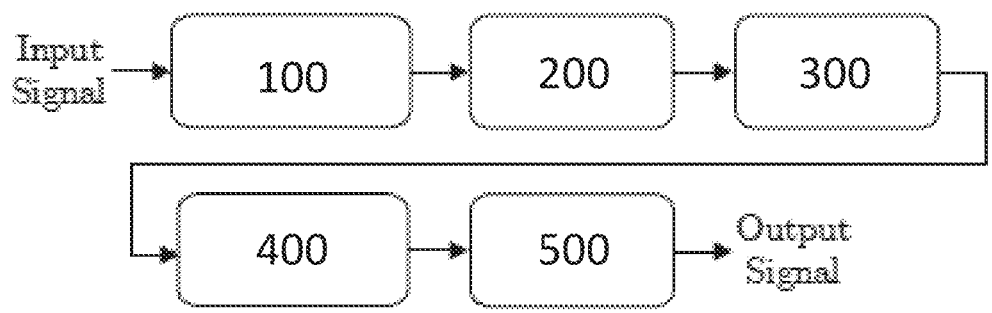
FIG. 1 schematically depicts an overall structure of the present system.

Turning to FIG. 1, the present system basically includes a signal pre-processor 100, an epoch generator 200, a feature extractor 300, a classifier 400, and a predictor 500. When the EEG signal generated from the brain of a subject is detected by an EEG electrode or alike (not shown in FIG. 1), it is initially pre-processed by the signal pre-processor 100, then processed by the following sequence of different levels in the present system: epoch generator, feature extractor, classifier and predictor. The signal inputted to and after processed by the present system will be outputted as a score of anesthetic state of the subject denoting the depth of anesthesia (DOA) of the subject.

Figure 2:
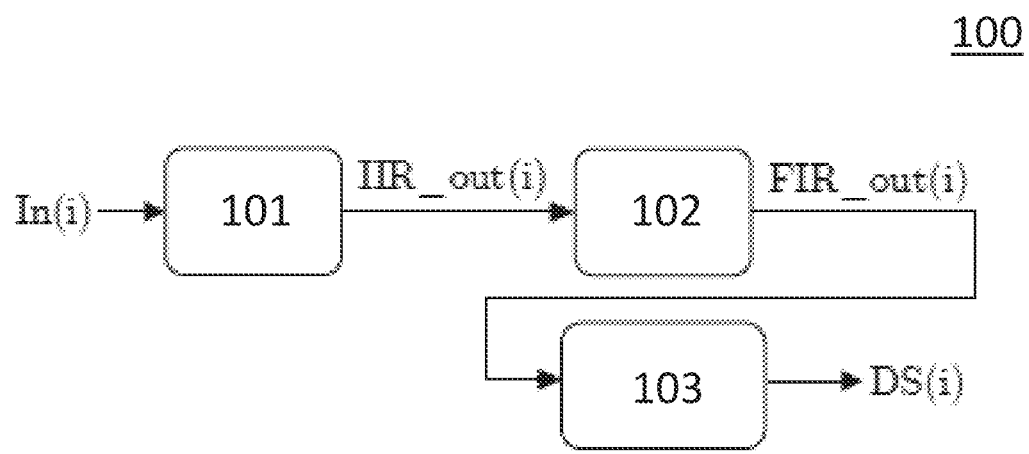
FIG. 2 schematically depicts the structure of a signal pre-processor according to an embodiment of the present invention.
Figure 3A:
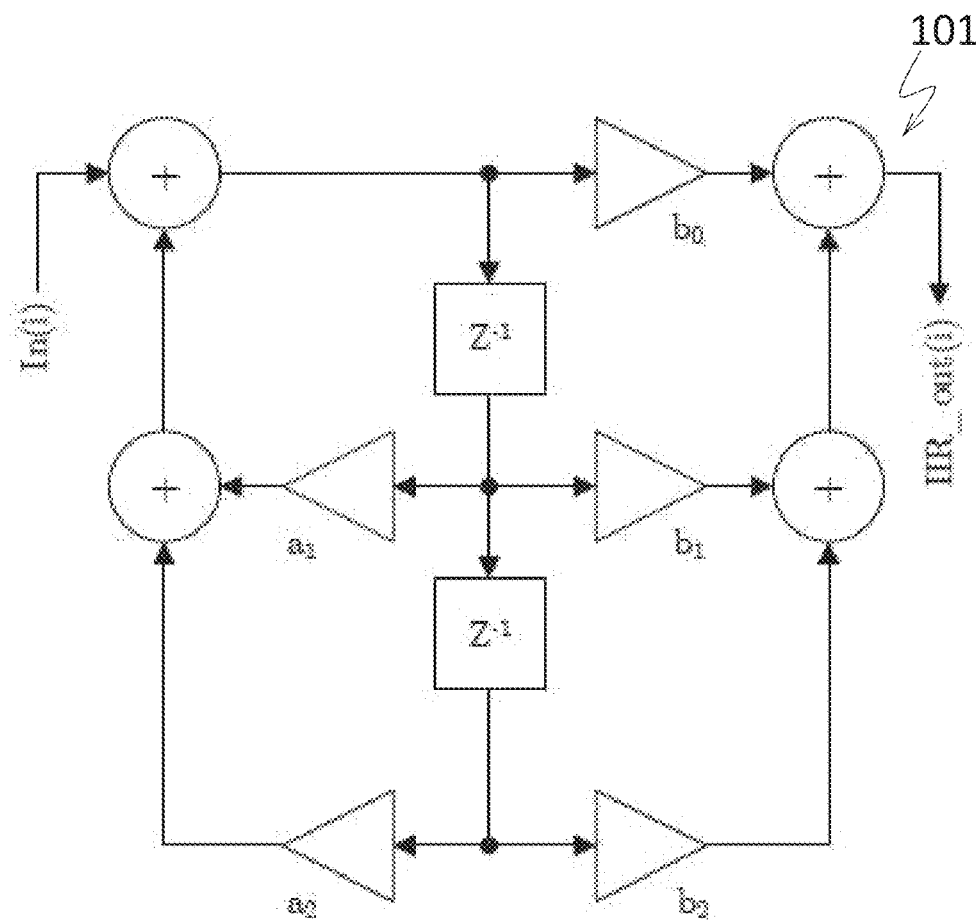
FIG. 3A schematically depicts the structure of a first filter (IIR filter) of the signal pre-processor as shown in FIG. 2.

Turning to FIG. 2, as a first level of the present system, the signal pre-processor includes two filters and a down sampler. A first filter 101, selected from a 50 Hz band-stop Infinite Impulse Response (IIR) filter, initially receives the EEG signal detected by an EEG electrode or alike from the subject. A 50 Hz band-stop IIR filter is selected for the first filter of the pre-processor is because the EEG collected from the brain of a small animal, e.g., mouse, has a very low voltage amplitude. The afore-mentioned band-stop frequency of the first filter can vary depending on the voltage amplitude of the EEG of a designated animal. Detailed circuitry diagram of the first filter is shown in FIG. 3A.

Figure 3B:
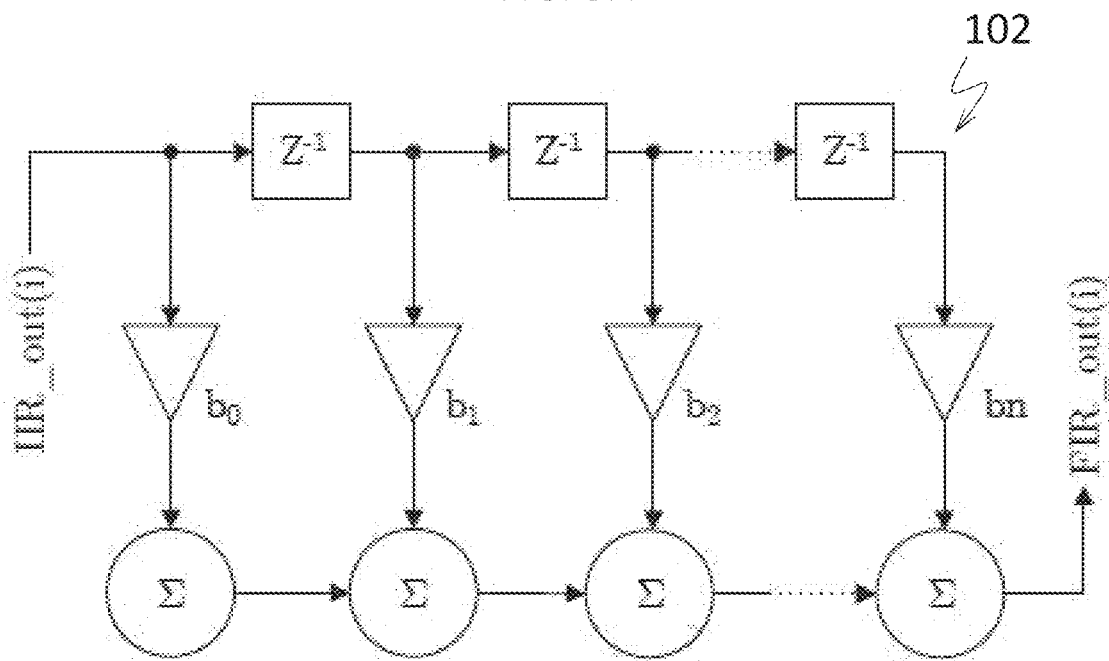
FIG. 3B schematically depicts the structure of a second filter (FIR filter) of the signal pre-processor as shown in FIG. 2.

A second filter 102, selected from a low-pass equiripple Finite Impulse Response (FIR) filter, is configured in the signal pre-processor subsequent to the first filter because the anesthetic effect on brain signal of small animal is only significant in the low-frequency region, and the low-frequency region is usually less than 250 Hz. In certain embodiments of the present invention, the incoming signal to the FIR filter is already passed through another low-pass filter with a cut-off frequency of 250 Hz. Employing the FIR filter with the same cut-off frequency is for reducing further unnecessary data from the signal, according to the Nyquist-Shannon sampling theorem which states that sampling at a rate which is twice as the highest significant frequency can represent the signal without any loss of information. Hence, in those embodiments, the sampling frequency can be up to 500 Hz. Detailed circuitry diagram of the second filter is shown in FIG. 3B.

Figure 3C:
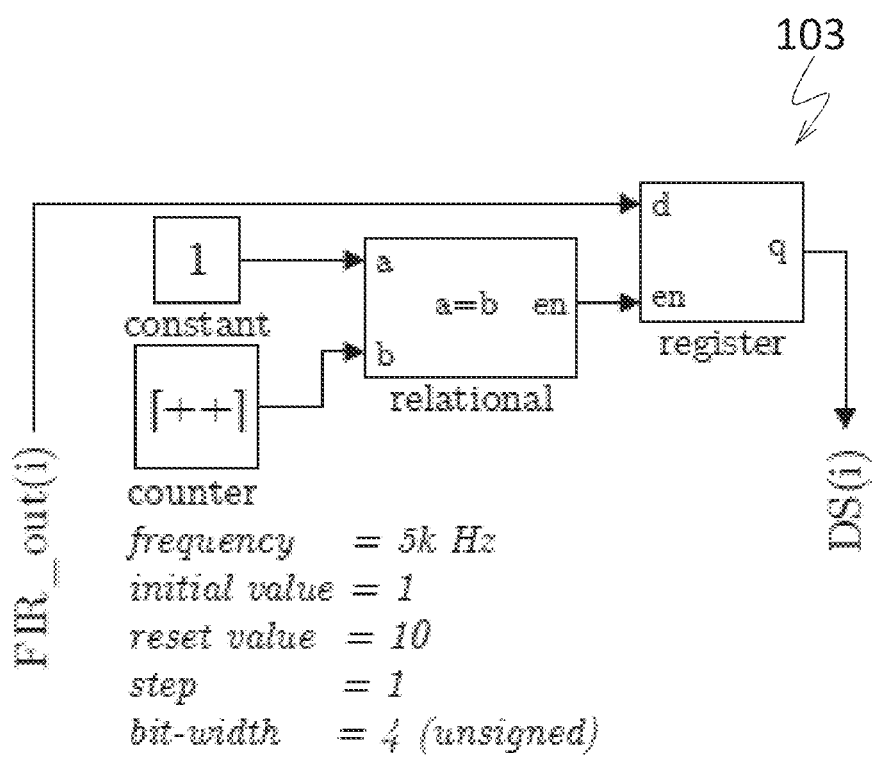
FIG. 3C schematically depicts the structure of a down sampler of the signal pre-processor as shown in FIG. 2.

A down sampler 103 is configured subsequent to the second filter in the signal pre-processor for down sampling the EEG signal received by the signal pre-processor. Taking a mouse EEG signal as an example, the sampling frequency is 5 KHz. According to the Nyquist-Shannon sampling theorem and the selected FIR filter cut-off frequency, the mouse EEG signal from this mouse model has to be down sampled 10 times (r=10) according to the architecture of the down sampler as shown in FIG. 3C. In FIG. 3C, the down sampler includes a count limited up counter which counts from 1 to 10, and repeats at the frequency of 5 KHz. When the counter value is equal to 1, the value of the input signal is stored in a register and kept as the output for the subsequent cycles.

Figure 4:
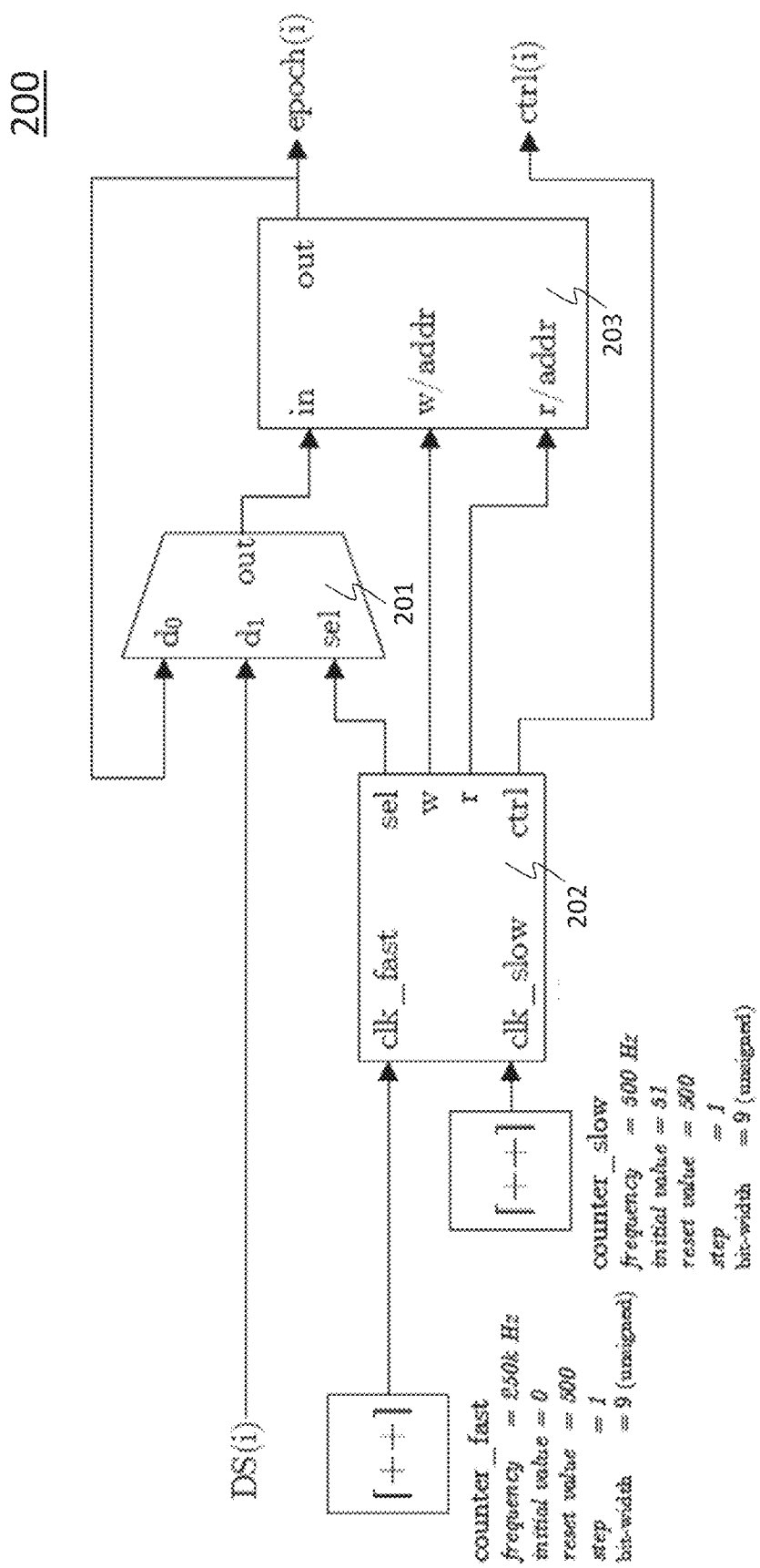
FIG. 4 schematically depicts the structure of an epoch generator according to an embodiment of the present invention.

Turning to FIG. 4, an epoch generator 200 is configured to consume lower resources and reduce the size of the memory 203 to the smallest. The epoch generator 200 creates a "sliding window" for 1-second and 10% overlapping epochs. As shown in FIG. 4, after pre-processing the incoming signal through the first filter, second filter and down sampler of the pre-processor sequentially according to certain embodiments of the present invention, a downsampler's output, DS(i), is fed as one of the three inputs (d1) of a two-input multiplexer 201 of the epoch generator 200. A second input (d0) is a feedback signal, epoch(i), from the memory 203 (e.g., RAM). An address generator 202 determines a selector input (sel) of the multiplexer 201, where there are two inputs of the address generator: one at 250 KHz (counter_fast) and the other at 500 Hz (counter_slow), in which counter_slow is an up counter that starts counting from 51 to 500 at 500 Hz frequency. The multiplexer's output is initially set as DS(i) until the counter value reaches 500. Once the multiplexer's output is equal to 500, counter_fast is activated and starts counting until the end of that cycle. During that time, the multiplexer's output is selected as epoch(i) and the counter_fast completes the counting from 1 to 500 at 250 KHz frequency. The output of the counter_slow and counter_fast are generated by the address generator as write address (w) and read address (r), respectively, which are further fed to the memory 203. The address generator 202 also generates a control signal, ctrl(i), for subsequent operations/processing. The output (out) of the multiplexer is an input data stream (in) of the memory. The output of the memory, epoch(i), together with ctrl(i), are fed into the feature extractor of the present system for further processing.

Figure 5:
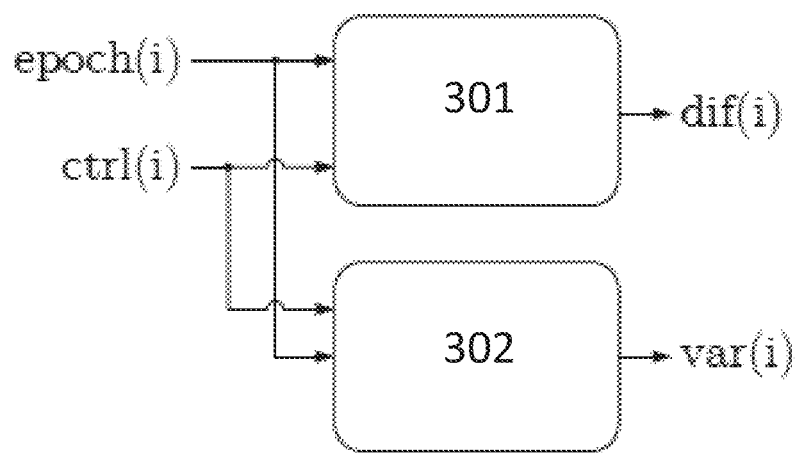
FIG. 5 schematically depicts the structure of a feature extractor according to an embodiment of the present invention.

Turning to FIG. 5, because two sets of features, derivative and variance, are needed to be extracted for the subsequent classification, both epoch(i) and control signal, ctrl(i), outputted from the epoch generator 200 are simultaneously fed into the feature extractor 300. The feature extractor 300 includes two distinct units: derivative calculator 301 and variance calculator 302, to respectively determine derivative, dif(i), and variance, var(i). Detailed circuitry diagrams of the derivative calculator 301 and variance calculator 302 are shown in FIG. 6A and FIG. 6B, respectively.

Figure 6A:
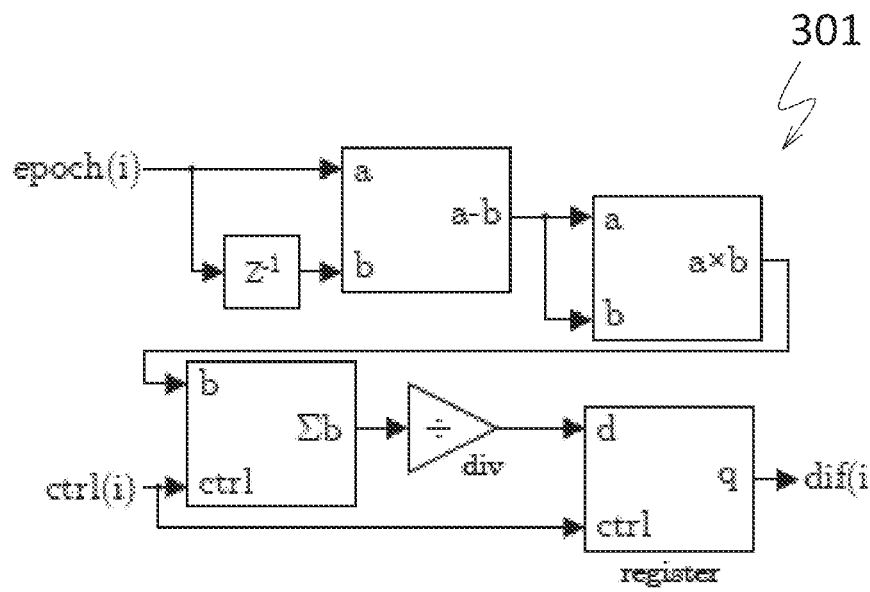
FIG. 6A schematically depicts the structure of a derivative calculator of the feature extractor as shown in FIG. 5.
Figure 6B:
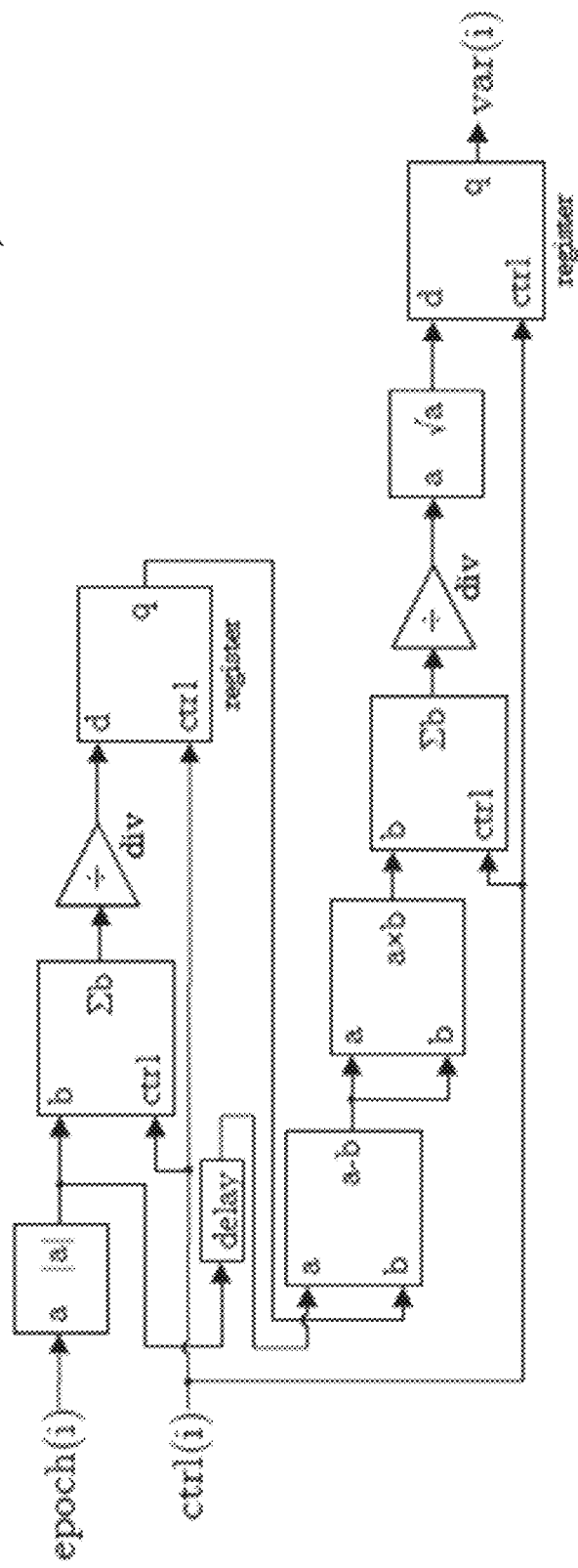
FIG. 6B schematically depicts the structure of a variance calculator of the feature extractor as shown in FIG. 5.

Turning to FIG. 6A, the derivative feature of the epoch signal is determined by the derivative calculator 301. A measure of a first-order derivative represents the rate of change in neural activity with respect to time. The neural activity increases in awake (conscious) state compared to anesthetic state. Determination of this derivative is a first feature to differentiate between the two states in terms of their neural activity variation, which is determined by calculating the mean of the accumulated squared-difference between each sample and its preceding one according to the following equation (1):

$$X_l(i) = \text{mean}\left[\left(\frac{dx_i}{dt}\right)^2\right] \qquad (1)$$

where $X_1(i)$ is the derivative feature for $i^{th}$ EEG epoch $x_i(t)$.

The first derivative is squared before computing the mean to avoid the result be zero and give a single concrete positive measure. To implement in the derivative calculator, the following equation (5) is given:

$$\text{derivative}, \text{dif}(i) = \text{mean}[(\text{epoch}(i) - \text{epoch}(i-1))^2] \quad (5)$$

In FIG. 6A, a delay is used, along with a subtractor, to calculate the difference between two epochs. After that, a multiplier is used to perform the square operation. An accumulator and a divisor are used to calculate the mean thereafter. Finally, with the help of the control signal, ctrl(i), the derivative, dif(i), is stored in a register for subsequent classification.

Turning to FIG. 6B, a variance of a series of epochs of both states is determined by the square root of the squared epoch according to equation (2):

$$\sigma = \sqrt{\frac{\sum_{i=1}^{N}(x_i^+ - \mu^+)^2}{N}} \quad (2)$$

where $x_i^+ = \sqrt{x_i^2}$ and $\mu^+$ is an average of $x_i^+ \cdot \sigma$ and N represents population variance and size of each successive epoch.

Considering the absolute value of epoch amplitude, mean, $\mu$, can be determined by equation (6):

$$\text{mean}, \mu = \frac{1}{n}\sum_{i=1}^{n}|\text{epoch}(i)|; \quad (6)$$

and variance, var(i), can be determined by equation (7):

$$\text{Variance}, \text{var}(i) = \sqrt{\frac{1}{n}\sum_{i=1}^{n}(|\text{epoch}(i)| - \mu)^2} \quad (7)$$

In FIG. 6B, the absolute value of each epoch is accumulated and divided by the epoch's total sample number to determine the mean. The mean is subtracted from epoch(i) to determine its deviation. An average of the squared deviation is determined by consecutively using a multiplier, an accumulator, and a divisor circuit. Finally, the square root of the average squared deviation is obtained, which is variance, var(i). Variance, var(i), is stored in a register for subsequent classification.

Figure 7:
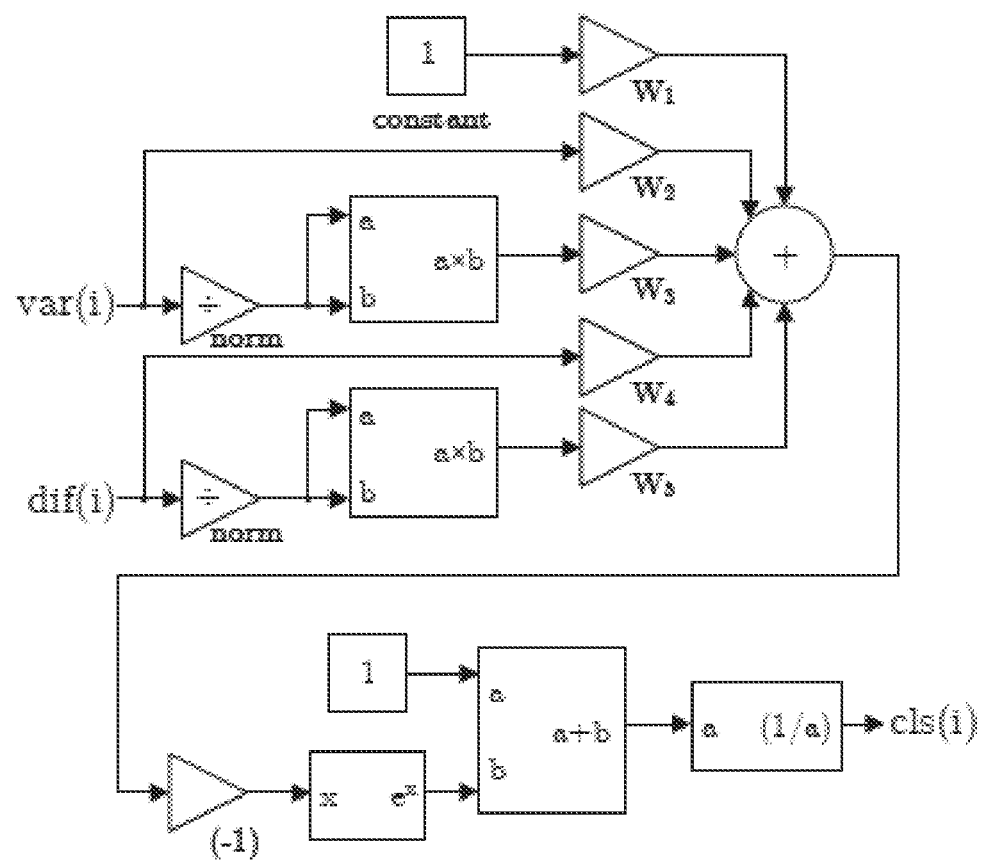
FIG. 7 schematically depicts the circuitry structure of a classifier according to an embodiment of the present invention.

Turning to FIG. 7, the two features, variance, var(i), and derivative, dif(i), extracted by the feature extractor 300 and stored in the respective register of the variance calculator 302 and derivative calculator 301 are inputted into the classifier 400 to implement a logistic regression classification which is an efficient and hardware-friendly machine learning algorithm for multiclass classification. The classifier 400 comprises two main cascaded units. A first unit is a feature mapping unit for expanding all features by double the number of the features, where the features doubled include original features and corresponding squared values. By feature mapping, classification accuracy is enhanced due to a better classification boundary produced by an increase in classifier variance. A second unit is a sigmoid function that is fed by the output of the feature mapping unit to serve as a decision boundary, which is implemented by an exponential and reciprocal computation circuit for subsequent prediction. The sigmoid function, $f(x)$, is according to equation (3):

$$f(x) = \frac{1}{1 + e^{-(\beta x)}} \quad (3)$$

In FIG. 7, $W_1$-$W_5$ are regression weights which are multiplied with the inputs and their squared values by the feature mapping unit before being fed to the exponential and reciprocal computation circuit. If the output of the classifier, cls(i), is lower than 0.5, the epoch will be classified as awake (conscious) state; otherwise, anesthetized state.

To get a highly accurate and fast prediction of EEG channels, a prediction mechanism based on accumulation of classifier outputs for consecutive EEG epochs is implemented in the predictor 500. In particular, the predictor 500 is configured to accumulate the classifier's outputs and constrains the result between 0 and 1. It initially starts with a decision value of 0.5 (i.e., 50%), meaning both awake and anesthetized classes have the same probability. The classifier's output of each received segment leads the prediction decision either up or down according to equation (4):

$$P_{pred}(i) = \text{satlin}[P_{pred}(i-1) + (2f(x_i) - 1)B] \quad (4)$$

where i=1: number of epochs, $P_{pred}(0)=0.5$, B=0.05 (jump bound), and satlin is a saturating linear transfer function to keep the predictor output out(i) bounded within 0 and 1.

Successive anesthetized or awake segments accumulate the prediction probability ($P_{pred}$) upward or downward, respectively, with scaled steps. A confident prediction decision is achieved after crossing the anesthetized (75%) or awake (25%) decision threshold. By this mechanism, a confident prediction decision of 100% channel prediction accuracy for all datasets can be guaranteed.

Figure 8:
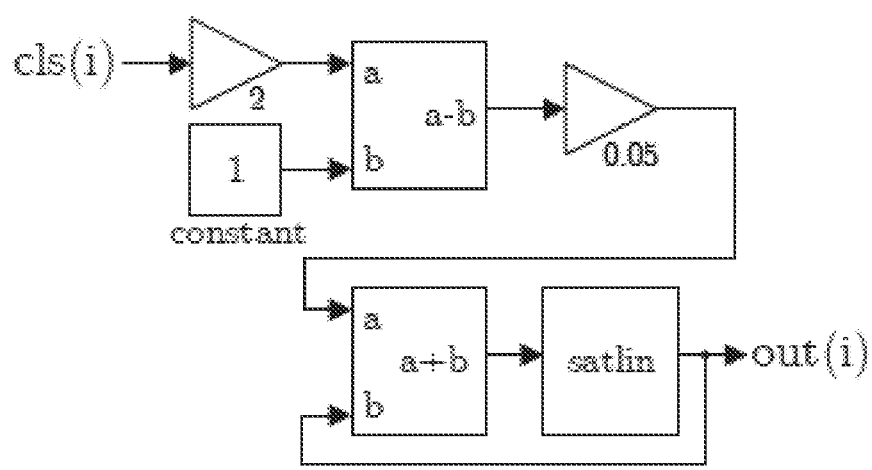
FIG. 8 schematically depicts the circuitry structure of a predictor according to an embodiment of the present invention.

Turning to FIG. 8, the predictor 500 includes a predictor circuit configured to determine the level of anesthesia according to equation (8) which is derived from equation (4):

$$\text{out}(i) = \text{satlin}[\text{out}(i-1) + (2*cls(i) - 1)*0.05] \quad (8)$$

where satlin is the saturating linear transfer function which helps follow the transient behavior of the EEG instantly, i.e., to track immediately if a subject is waking up from anesthesia. This function also helps obtain a meaningful interpretation of the output level in terms of decimal values of percentages; out(i) denotes the measured DOA.

EXAMPLE

Example 1

Table 1 below summarizes performance of the present system by using multiple classes of testing datasets to measure the accuracy of the present system. In this example, all datasets have been pre-processed to generate 1-second epochs with 10% overlapping before being subject to classification.

TABLE 1

| Set | Class | Duration (s) | Total Epochs | C.C.# Epochs | Class Accuracy | C.P.D.^ Time (s) |
|---|---|---|---|---|---|---|
| 1 | Anesth. | 600 | 666 | 644 | 96.70% | 6.5 |
| 2 | Anesth. | 600 | 666 | 594 | 89.19% | 6.4 |

TABLE 1-continued

| Set | Class | Duration (s) | Total Epochs | C.C.[#] Epochs | Class Accuracy | C.P.D.[^] Time (s) |
|---|---|---|---|---|---|---|
| 3 | Anesth. | 600 | 666 | 635 | 95.35% | 6.8 |
| 4 | Anesth. | 600 | 666 | 645 | 96.85% | 6.5 |
| 5 | Anesth. | 600 | 666 | 638 | 95.80% | 6.6 |
| 6 | Anesth. | 600 | 666 | 623 | 93.54% | 7.9 |
| 7 | Anesth. | 600 | 666 | 640 | 96.10% | 6.2 |
| 8 | Anesth. | 600 | 666 | 577 | 86.64% | 7.3 |
| 9 | Anesth. | 600 | 666 | 543 | 81.53% | 8.1 |
| 10 | Anesth. | 600 | 666 | 592 | 88.89% | 7.3 |
| 11 | Awake | 600 | 666 | 650 | 97.60% | 4.6 |
| 12 | Awake | 600 | 666 | 654 | 98.20% | 4.6 |
| 13 | Awake | 600 | 666 | 655 | 98.35% | 4.6 |
| 14 | Awake | 600 | 666 | 654 | 98.20% | 4.5 |
| 15 | Awake | 600 | 666 | 651 | 97.75% | 5 |
| 16 | Awake | 600 | 666 | 619 | 92.94% | 10 |
| 17 | Awake | 600 | 666 | 622 | 93.39% | 10 |
| 18 | Awake | 600 | 666 | 598 | 89.79% | 11 |
| 19 | Awake | 600 | 666 | 647 | 97.15% | 4.6 |
| 20 | Awake | 600 | 666 | 652 | 97.90% | 4.6 |
| 21 | Trans. | 400 | 446 | 412 | 92.38% | 14.9 |
| 22 | Trans. | 400 | 446 | 433 | 97.09% | 7.9 |
| 23 | Trans. | 400 | 446 | 426 | 95.52% | 6.6 |
| 24 | Trans. | 400 | 446 | 412 | 92.38% | 12.4 |

Keys:
[#]Correctly Classified Epochs
[^]Confident Prediction Decision Time
"Anesth.": Anesthetized
"Trans.": Transition, i.e., From Anesthetized to Awake to Anesthetized In cases of completely anesthetized subjects, the classification accuracy is about 92% on average; those from awake subjects result in about 96% average classification accuracy; those from transition subjects result in about 94% average classification accuracy. To reach 100% channel prediction accuracy, the present system takes about 7 seconds on average. The accuracy found in this example suggests that the DOA obtained by the present system in multiple classes is comparable to a clinical-level accurate DOA, or even more accurate.

Example 2

Table 2 below summarizes the resource utilization of the present invention incorporated into a conventional FPGA (Xilinx Artix-7 FPGA is selected in this example)

TABLE 2

| Resource | Available | Utilized | Utilization Rate |
|---|---|---|---|
| LUT | 53200 | 18522 | 34.82% |
| LUTRAM | 17400 | 33 | 0.19% |
| FF | 106400 | 876 | 0.82% |
| BRAM | 140 | 2 | 1.43% |
| DSP | 220 | 54 | 24.55% |

Keys:
"LUT": Look Up Table
"LUTRAM": LUT Random-Access Memory
"FF": FlipFlop
"BRAM": Block RAM
"DSP": Digital Signal Processing Blocks The results from Table 2 suggests that the present invention consumes lower level of resources in different aspects compared to some conventional hardware-implemented DOA systems, such as Saadeh et al. (2019), in which it requires six feature extraction and uses the fine-decision-tree classification algorithm (requiring 26,520 FFs; 50,111 LUTs) for measuring DOA. In contrast, the present invention uses a simple logistic regression machine learning algorithm for classification; the present invention only requires 876 FFs and 18,522 LUTs in FPGA, because only two features are required to be extracted, and the features selected are hardware-friendly and mathematically uncomplicated. One more advantage of the present invention over the conventional DOA measurement system is a relatively lower on-chip power consumption (only 0.446 watts including 0.338 watts of dynamic and 0.108 watts of static power, respectively) because a 28 mm CMOS chip is used. An average total system delay of the datasets is about 12 µs which is mainly due to the inherent properties of the FIR filter used in the signal pre-processor. This latency is within the tolerance of measuring EEG of small animal. If this system latency needs to be shortened to fit other models or purposes, it can be further reduced by using an alternative analog equivalent to the FIR filter of the signal pre-processor.

Figure 9A:
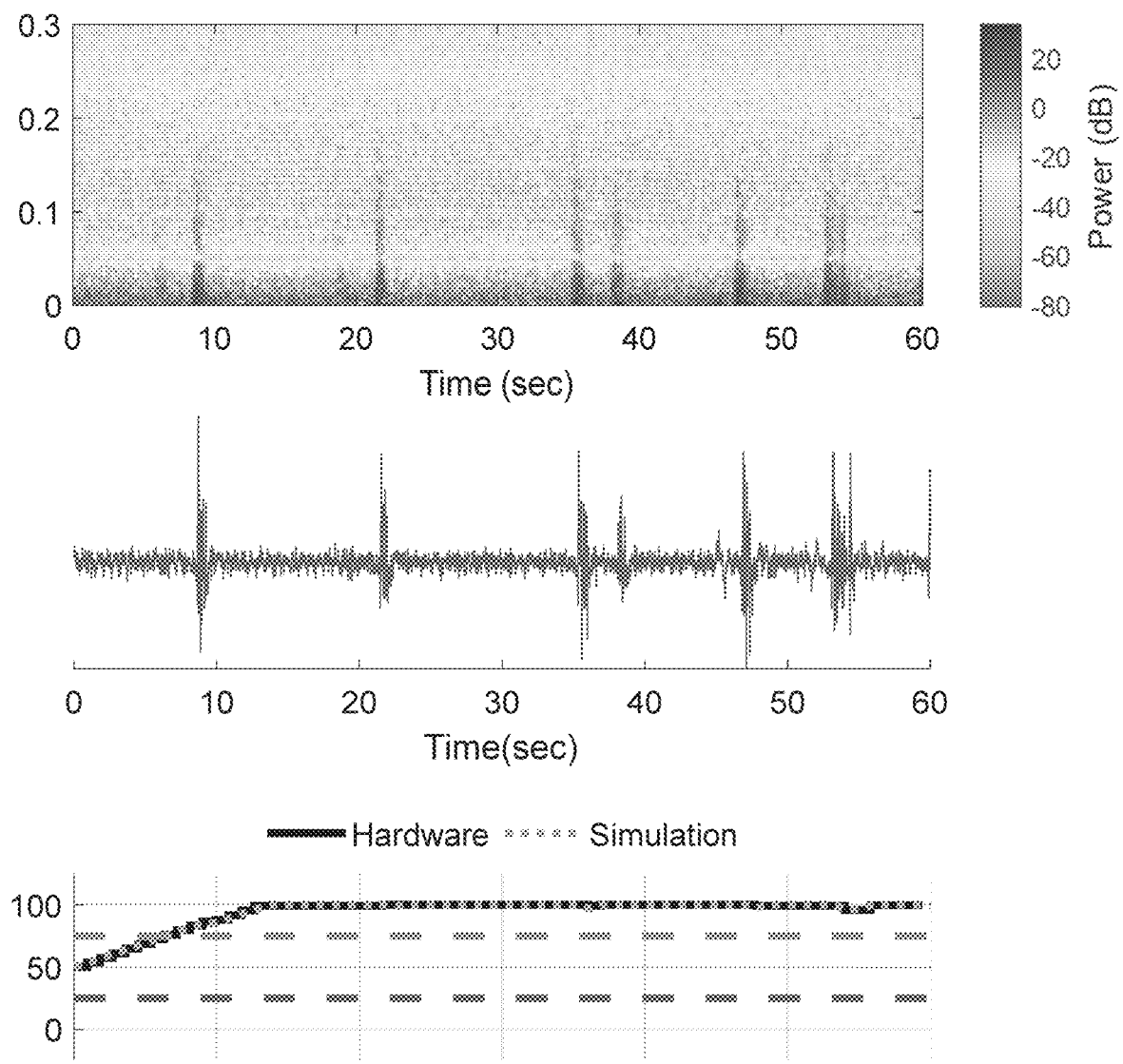
FIG. 9A shows the comparison between a model simulation and output of the present system in an anesthetized animal model: top panel is spectrogram; middle panel is electroencephalogram; bottom panel shows prediction of superimposed waveforms of simulated and hardware outputs.
Figure 9B:
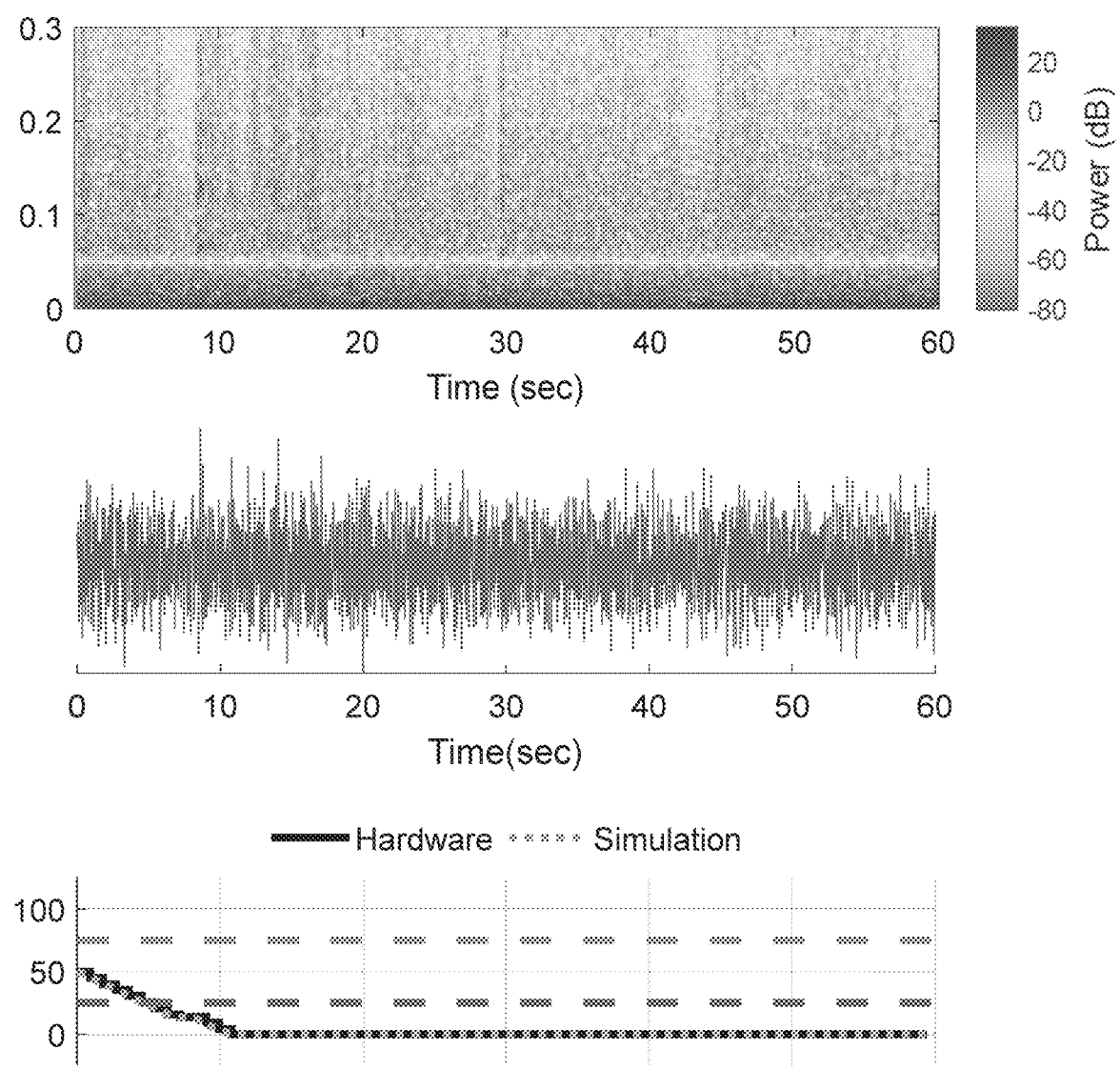
FIG. 9B shows the comparison between a model simulation and output of the present system in a conscious (awake) animal model: top panel is spectrogram; middle panel is electroencephalogram; bottom panel shows prediction of superimposed waveforms of simulated and hardware outputs.
Figure 9C:
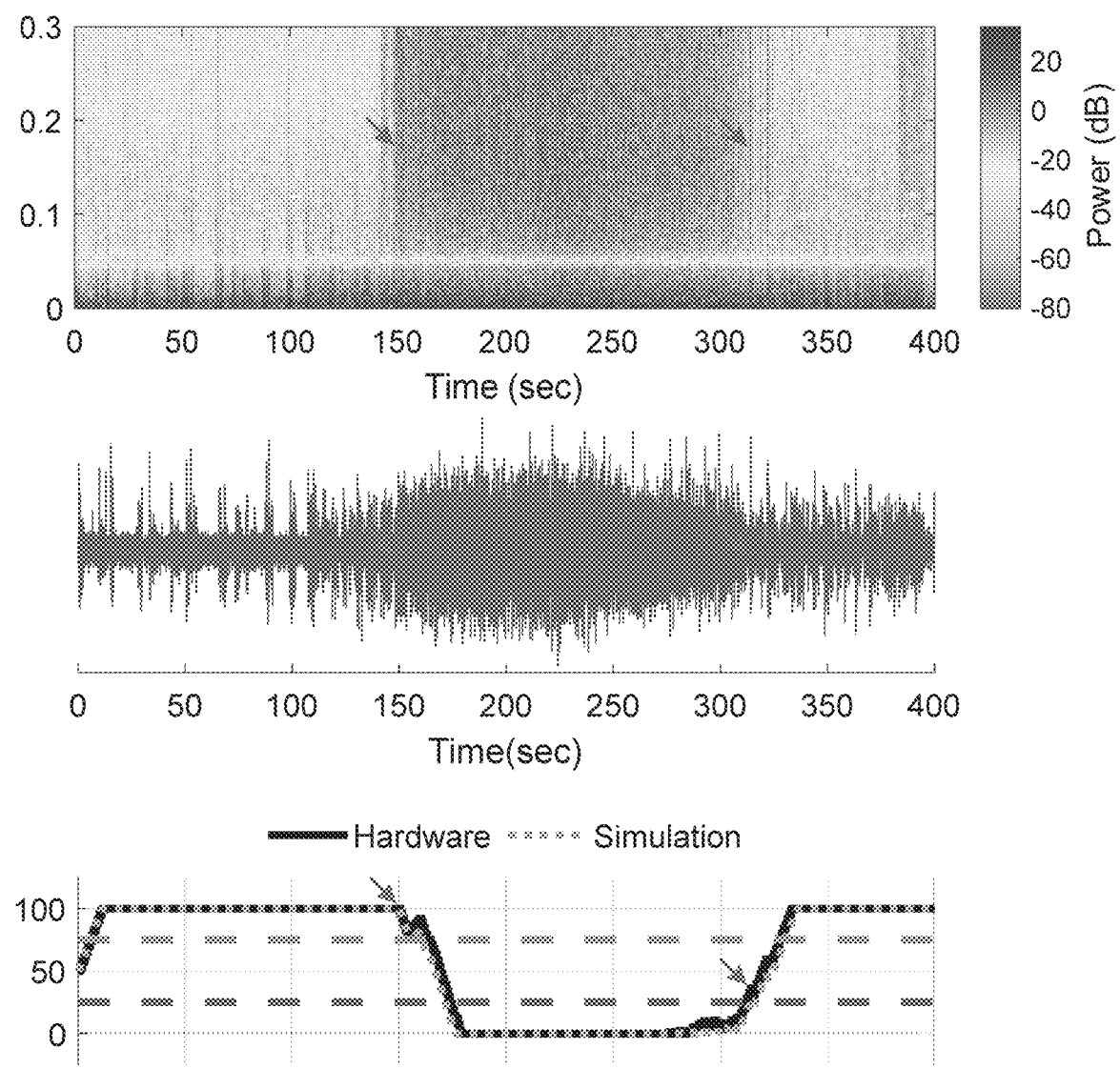
FIG. 9C shows the comparison between a model simulation and output of the present system in an animal model during transition (conscious/anesthetic cycle): top panel is spectrogram; middle panel is electroencephalogram; bottom panel shows prediction of superimposed waveforms of simulated and hardware outputs.

FIGS. 9A-9C provides spectrogram, electroencephalogram and prediction by superimposing output waveforms of a simulation and a hardware output in three different classes, respectively. In the top panel of each of FIGS. 9A-9C, the corresponding spectrogram provides a way to observe a temporal EEG in a spectral domain. For example, the dominant power of anesthetized EEG is in the lower frequency spectrum (top panel in FIG. 9A). On the other hand, the power is distributed in the higher frequency oscillation region in awake EEG cases (top panel in FIG. 9B). The spectrogram from the transition EEG cases is especially remarkable in terms of giving class alteration boundary (marked by two arrows in top and middle panels of FIG. 9C). From the superimposed output waveforms (bottom panel in each of FIGS. 9A-9C) which provides a mean of graphical comparison between simulated and hardware-generated results, respectively, it can be seen that the two output traces are extensively identical in all three classes, suggesting that the present system is capable of measuring DOA substantially in line with the simulated result from a corresponding software running the same algorithm.

Figure 10A:
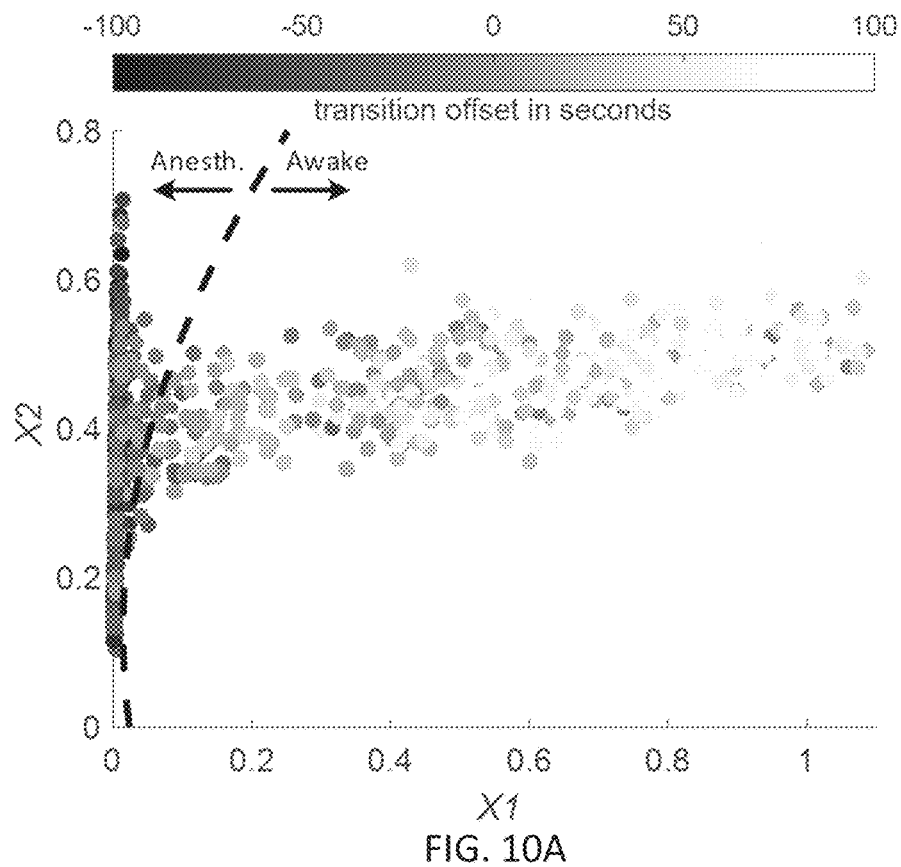
FIG. 10A shows a time-coded scatter plots of features for transition cases as shown in FIG. 9C, where the subjects pass from anesthetized to awake state.
Figure 10B:
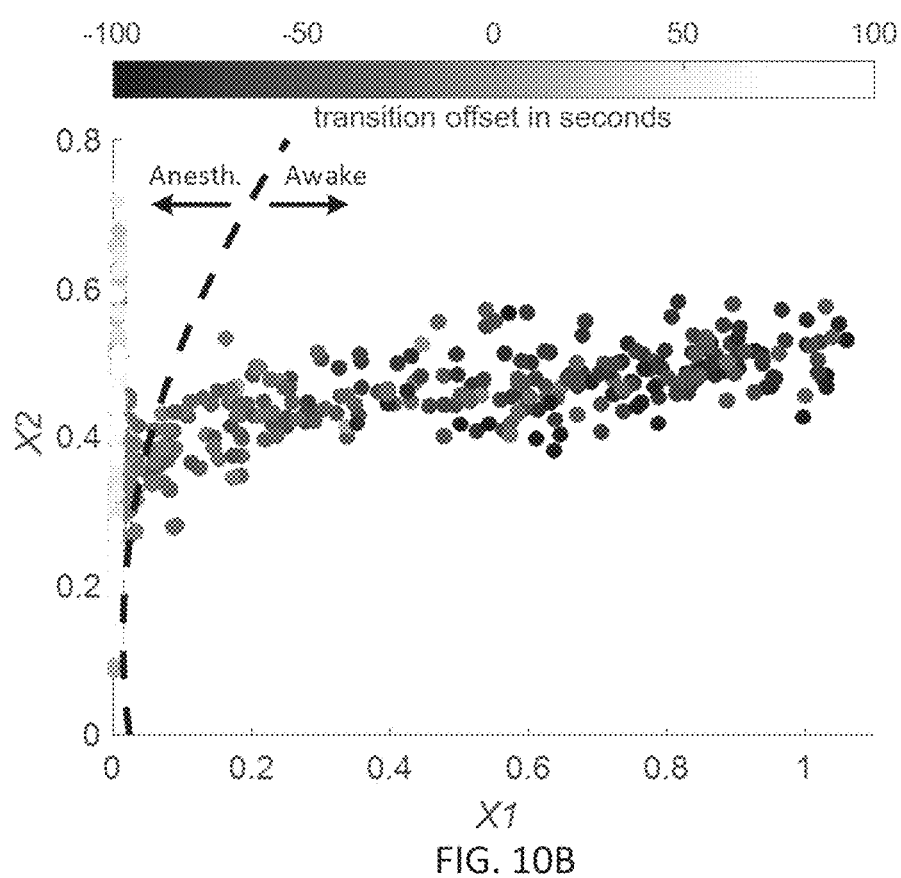
FIG. 10B shows a time-coded scatter plots of features for transition cases as shown in FIG. 9C, where the subjects pass from awake to anesthetized state.

To illustrate a gradient shift of properties in feature space, FIGS. 10A and 10B provide time-coded scatter plots of features by taking the transition cases according to FIG. 9C as an example. Corresponding dotted line in FIGS. 10A and 10B represent the decision boundary separating two classes (anesthetized and awake). From the plots in FIGS. 10A and 10B, it is evident that the measures of the associated features according to the present invention go through a gradient transition from one class to another in those transition cases, which validates the incremental DOA measurement according to the present invention.

Table 3 below summarizes the difference(s) between the conventional DOA measurement methods and the present invention.

TABLE 3

| | Signal Used | Subject | No. of features extracted | Classification Method | Classification Accuracy | Sensitivity | Specificity | Hardware? | CMOS? | Power Requirement |
|---|---|---|---|---|---|---|---|---|---|---|
| Liu et al. (2018) | EEG | Human | 1 | Random Forest | 70.78% | Not available | Not available | No | Not available | Not available |
| Nagaraj et al. (2018) | EEG | Human | 6 | SVM | 81.18% | 81.30% | 81.06% | No | Not available | Not available |
| Shalbaf et al. (2018) | EEG | Human | 4 | ANFIS-LH | 93.00% | Not available | Not available | No | Not available | Not available |
| Ha et al. (2018) | EEG, NIRS | Human | 10 | DNN | Not available | Not available | Not available | Yes | 65 mm | 1.0 V |
| Khan et al. (2018) | EEG, EMG | Human | 7 | S. Decision Tree | 79.00% | 83.40% | 74.6% | Yes | 65 mm | 1.0 V |
| Saadeh et al. (2019) | EEG | Human | 6 | F. Decision Tree | 92.20% | 91.90% | 92.06% | Yes | 65 mm | 0.90 V |
| Yoon et al. (2011) | EEG | Animal | 1 | Mod. Shamnon | Not available | Not available | Not available | No | Not available | Not available |
| Kortelainen et al. (2012) | EEG | Animal | 1 | Bayesian Info. | Not available | Not available | Not available | No | Not available | Not available |
| Xu et al. (2005) | EEG | Animal | 1 | Lempel-Ziv | Not available | Not available | Not available | No | Not available | Not available |
| Present Invention | EEG | Animal | 2 | Logistic Regression | 94.00%# or 100.00%^ | 92.06%# | 95.06% | Yes | 28 mm | 0.95 V |

Classification for 1-second Epoch
^Channel prediction after an average 7 second run-time It can be seen that most of the conventional DOA measurement methods are for human subjects; their classification accuracy only ranges from 70% to 93%. There is no hardware-implemented DOA measurement for smaller animal subjects, but only software-based conventional methods are available with relatively low classification accuracy. Most of the conventional DOA measurement methods with hardware implementation use 65 mm CMOS chips, whereas only 28 mm CMOS chip is used in the present invention to enable a better FPGA performance.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

INDUSTRIAL APPLICABILITY

The present invention provides a hardware-implemented DOA measurement based on EEG of small animal with high classification accuracy and channel prediction accuracy within a tolerable system latency, which has potentials in applying to veterinary medicine and surgery requiring anesthesia to an animal subject during surgical operation. It also has potentials to other operations at other settings requiring anesthesia or in observing change in other physiological parameters during transition from anesthesia to conscious state or vice versa of a subject.

The invention claimed is:

1. A device for assessing anesthesia of an animal subject in real-time from electroencephalography (EEG) measurements of the animal subject during application of anesthesia, the device comprising:

a signal pre-processor comprising a first filter with a first filtering frequency band, a second filter with a second filtering frequency band, and a down-sampler to pre-process sequentially an incoming measured EEG signal from the EEG measurements of the animal subject;
wherein the pre-processing comprises:
  removing unwanted signals and noise from the incoming measured EEG signal using the first filter and the second filter to generate a filtered incoming measured EEG signal; and
  down-sampling the filtered incoming measured EEG signal by the down-sampler to generate a down-sampled filtered incoming measured EEG signal;
an epoch generator configured to generate an epoch signal containing epochs of 1-second epoch duration each and 10% overlapping of consecutive epochs;
wherein the epoch generator comprises a two-input multiplexer, an address generator, and a memory;
wherein the two-input multiplexer is configured to:
  receive the down-sampled filtered incoming measured EEG signal, a feedback of the epoch signal, and a selector input from the address generator; and
  generate a multiplexer output from the down-sampled filtered incoming measured EEG signal or the feedback of the epoch signal based on the selector input;
wherein the address generator comprises:
  a slow counter configured to generate write addresses, and count from a slow counter start count to a slow counter end count in repeating slow count cycles; and
  a fast counter configured to generate read addresses, and count from a fast counter start count to a fast counter end count in repeating fast count cycles that starts after each of the slow count cycles;
wherein the slow counter is further configured to repeat each of the slow count cycles after each of the fast count cycles;
wherein the fast counter is further configured to repeat each of the fast count cycles after each of the slow count cycles;

wherein the address generator is further configured to:
generate the selector input to the multiplexer to generate the multiplexer output from the down-sampled filtered incoming measured EEG signal during each of the slow count cycles and from the feedback of the epoch signal during each of the fast count cycles;

wherein the epoch generator is configured to:
receive the multiplexer output, the write addresses, and the read addresses;
store the received multiplexer output as data according to the received write addresses; and
retrieve data according to the received read addresses and output the retrieved data as a memory output;

wherein the epoch generator is configured to generate the epoch signal and output the epoch signal from the memory output;

a feature extractor configured to:
receive the epoch signal from the epoch generator;
extract a derivative feature of each epoch of the received epoch signal by computing a mean of accumulated squared-differences among epochs in the received epoch signal; and
extract a variance feature of each epoch of the received epoch signal by computing a square root of an average squared-deviation of epochs in the received epoch signal;

a classifier configured to:
perform a feature mapping on each derivative feature and each variance feature to its original value and its squared value; and
for each epoch of the received epoch signal, set a classification boundary from an output of the respective feature mappings to generate a classifier output for the epoch the classifier output being either that the animal subject is awake or that the animal subject is anesthetized; and a predictor comprising a predictor circuit configured to:
accumulate a plurality of the classifier outputs corresponding to the epochs of the received epoch signal; and and
predict a likelihood of the animal subject being under anesthesia state from the accumulated classifier outputs.

2. The system of claim 1, wherein the first filter of the signal pre-processor is configured to filter the incoming measured EEG signal at the first filtering frequency band to reduce a power-line interference of the incoming measured EEG signal.

3. The system of claim 1, wherein the second filter of the signal pre-processor is configured to low-pass filter the incoming measured EEG signal at the second filtering frequency band to remove signal components in the incoming measured EEG signal that do not fall within an electroencephalography frequency band of interest.

4. The system of claim 1, wherein the incoming measured EEG signal is down sampled at least ten times after being subjected to the second filter using the down-sampler.

5. The system of claim 1, wherein the computing of a mean of accumulated squared-differences among the epochs in the received epoch signal comprises:
computing a difference between two consecutive epochs of the epochs in the received epoch signal and a square of the difference to obtain a squared difference;
repeating the computation to obtain a squared difference for each pair of consecutive epochs in the received epoch signal;
accumulating all of the squared differences obtained; and
determining the mean of the accumulated squared differences.

6. The system of claim 1, wherein the computing of a square root of an average squared-deviation of the epochs in the received epoch signal comprises:
obtaining an absolute epoch value of each of the epochs in the received epoch signal;
accumulating all of the absolute epoch values obtained;
determining a mean of the accumulated absolute epoch values;
computing a difference between each of the absolute epoch values and the mean of the accumulated absolute epoch values and a square of each difference to obtain squared deviations;
computing an average of all of the squared deviations for all of the absolute epoch values; and
computing a square root of the average of all of the squared deviations.

* * * * *